United States Patent
van den Berg

(12) 
(10) Patent No.: US 6,439,162 B1
(45) Date of Patent: Aug. 27, 2002

(54) UNMANNED VEHICLE TO BE USED IN A STABLE OR A MEADOW

(75) Inventor: Karel van den Berg, BR Bleskensgraaf (NL)

(73) Assignee: Lely Research Holding A.G., Zug (CH)

( * ) Notice: Subject to any disclaimer, the term of this patent is extended or adjusted under 35 U.S.C. 154(b) by 0 days.

(21) Appl. No.: 09/765,386

(22) Filed: Jan. 22, 2001

Related U.S. Application Data

(63) Continuation of application No. PCT/NL00/00308, filed on May 10, 2000.

(30) Foreign Application Priority Data

May 25, 1999 (NL) .............................................. 1012137

(51) Int. Cl.[7] .............................................. A01K 29/00
(52) U.S. Cl. ..................................... 119/174; 119/908
(58) Field of Search ............................... 119/174, 172, 119/719, 720, 908, 57.92

(56) References Cited

U.S. PATENT DOCUMENTS

| | | | | |
|---|---|---|---|---|
| 4,854,328 A | * | 8/1989 | Pollack ........................ | 119/174 |
| 5,474,085 A | * | 12/1995 | Hurnik et al. ............... | 119/174 |
| 5,791,294 A | * | 8/1998 | Manning ..................... | 119/908 |
| 5,816,192 A | * | 10/1998 | van der Lely et al. ..... | 119/57.92 |
| 6,043,748 A | * | 3/2000 | Touchton et al. ........... | 119/908 |
| 6,142,102 A | * | 11/2000 | Mack et al. ................. | 119/720 |
| 6,271,757 B1 | * | 8/2001 | Touchton et al. ........... | 119/908 |

FOREIGN PATENT DOCUMENTS

FR 2586223 * 4/1985 ................. 119/174

\* cited by examiner

*Primary Examiner*—Charles T. Jordan
*Assistant Examiner*—Elizabeth Shaw
(74) *Attorney, Agent, or Firm*—Penrose L. Albright

(57) ABSTRACT

An unmanned vehicle for use in a stable such as a cowshed or for use in a meadow or for use in both which is provided with detection components for determining the health and behavior of the animals in the stable or meadow. The detection components comprise an animal identification system including a radar and an infrared camera. The animals are fitted with identifying reflectors. The vehicle also has a herd control element for herding animals and for segregating one or more of the animals from other animals in the herd. Also the vehicle includes an extendible disinfecting member for disinfecting at least portions of the stable as well as parts of animals in the stable or meadow. An alarm is provided on the vehicle for alerting an operator that an animal is ill or acting abnormally. The vehicle also carries a mechanism to analyze manure on the stable floor.

24 Claims, 1 Drawing Sheet

UNMANNED VEHICLE TO BE USED IN A STABLE OR A MEADOW

RELATED APPLICATION

This Application is a continuation of International Application No. PCT/NL00/00308, May 10, 2000.

FIELD OF THE INVENTION

The invention relates to an unmanned vehicle to be used in a stable, such as a cowshed, or in a meadow.

BACKGROUND OF THE INVENTION

Known unmanned vehicles for use in stables are usually employed for cleaning stable floors.

SUMMARY OF THE INVENTION

It is an objective of the invention to provide a multifunctional, unmanned vehicle.

In accordance with the invention, this is achieved by providing an unmanned vehicle with detection means for determining the health or the behavior of animals or both. With the aid of its detection means the unmanned vehicle is capable of identifying animals which are ill or display abnormal behavior or both. According to an inventive feature, the unmanned vehicle comprises alarm means for informing a supervisor when an animal is ill or displays abnormal behavior. In this manner it is possible to react quickly and adequately when there is something wrong with an animal.

According to a further inventive feature, the detection means comprises an animal identification system provided with a transmitter and a receiver. By means of the animal identification system it is determined for example whether an animal is lying or standing longer than usually at a certain place. This may be an indication that the animal is ill. According to another inventive feature, the animal identification system comprises a radar as well as reflectors which react to the radar, such reflectors being disposed on the animals. Each of these reflectors has a unique code, so that it is possible to monitor the movements of each animal. In this manner it is also possible to determine abnormal behavior of the animals. According to another inventive feature, the detection means comprises a camera, preferably an infrared camera. By means of image analysis of the images of the animals recorded by the camera it is possible for example to determine whether an animal has mastitis or is injured or should be inseminated. It is also possible to track the animals by means of the camera. For enabling a still better view of the animals, the detection means are disposed on a telescopic carrier. According to again another inventive feature, the unmanned vehicle comprises herding means for controlling the animals. With the aid of the herding means animals can be separated from a group for the purpose of being inseminated or examined by a veterinary surgeon. In a preferred embodiment of the invention, the herding means comprises an electric shock device.

According to another aspect of the invention, the unmanned vehicle comprises disinfecting means for disinfecting at least a part of the stable or a part of an animal or both. According to again another aspect of the invention, the disinfecting means are disposed on-a telescopic carrier. The latter measure makes it possible to disinfect at places which are difficult to reach. For the purpose of making the unmanned vehicle still more multifunctional, it is provided with a manure slide for removing manure which is lying on a floor. According to another inventive feature, the unmanned vehicle is provided with navigation means for guiding the unmanned vehicle through the stable or the meadow. The navigation means may be the same as the above-described detection means.

BRIEF DESCRIPTION OF THE DRAWINGS

The invention will now be explained in further detail with reference to the accompanying drawings.

DETAILED DESCRIPTION OF THE PREFERRED EMBODIMENTS

Figure 1:
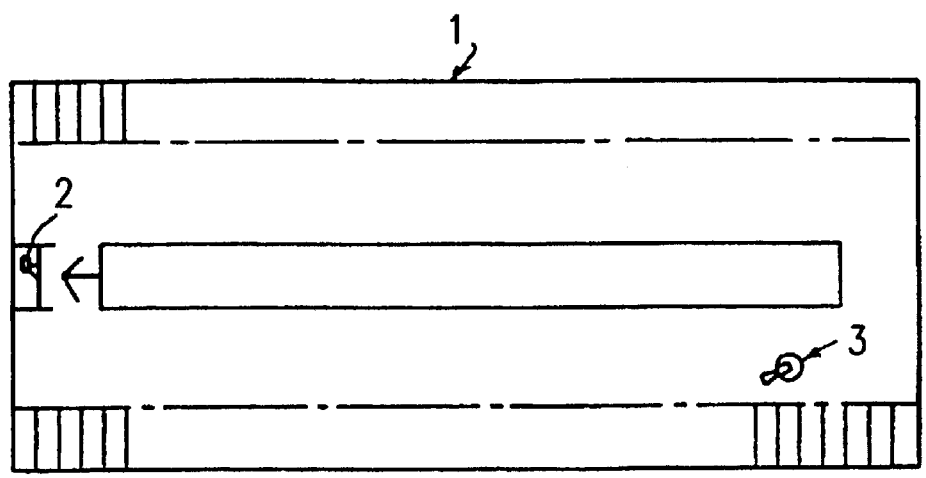
FIG. 1 is a plan view of a stable with an unmanned vehicle accommodated therein, which vehicle is provided with detection means according to the invention.

FIG. 1 is a plan view of a stable 1 provided with a milking robot 2 for automatically milking animals and an unmanned vehicle 3 which is provided with detection means 4 for determining the health or the behavior or both of animals.

Figure 2:
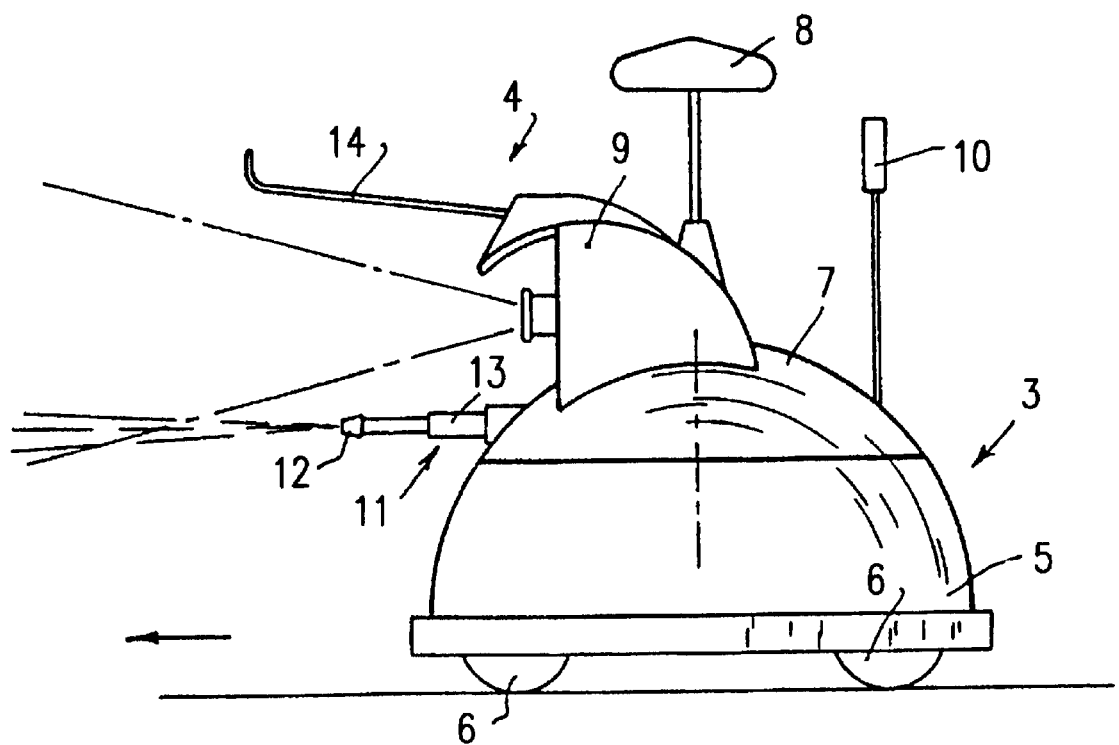
FIG. 2 is a side view of the unmanned vehicle shown in FIG. 1.

FIG. 2 is a side view of unmanned vehicle 3 according to the invention, which is provided with a chassis 5 with wheels 6. Wheels 6 are driven by a drive unit. A rotatable upper part 7 is arranged on chassis 5 on which detection means 4 are mounted. In the present embodiment detection means 4 comprises a radar 8 and a camera 9. Unmanned vehicle 3 is further provided with a transmitter unit including a transmitting element 10. By means of the transmitter unit a supervisor can be alerted when an animal is ill or displays abnormal behavior or both. On the rotatable upper part 7 a disinfecting means 11 is provided for disinfecting at least a part of the stable or at least a part of an animal or for carrying out both functions. In the present embodiment disinfecting means 11 comprises a sprayer 12 which is disposed on a telescopic carrier 13.

On rotatable upper part 7 an animal control means 14 is provided for herding animals. Control means 14 is fitted to the upper side of camera 9 and connected to an electric shock device which is capable of emitting an electrical pulse.

In the present embodiment camera 9 is used to guide the unmanned vehicle through a stable or a meadow or through both.

Although I have disclosed the preferred embodiments of my invention, it is to be understood that it is capable of other adaptations and modifications within the scope of the following claims:

Having disclosed my invention, what I claim as new and to be secured by Letters Patent of the United States of America is:

1. An unmanned vehicle which comprises detection means for sensing the state of health and abnormal behavior of individual animals in a herd of animals, and animal identification system for identifying individual animals in said herd of animals, said animal identification system comprising radar and distinctive individual reflectors worn by the animals in said herd of animals whereby each of said reflectors provide distinctive reflections which are received by said radar, and herding means for selectively segregating an animal from said herd of animals.

2. A vehicle in accordance with claim 1 in combination with a stable, the vehicle further comprising disinfecting means for disinfecting at least part of said stable and at least part of each said animal in said stable, a telescoping means for moving said disinfecting means relative to remaining parts of the vehicle, a manure slide means for removal of manure from a floor of said stable, signal means for alerting a supervisor wherein said detection means senses that an animal in said stable is ill or behaving abnormally, and a navigation means for directing the movement of the vehicle in said stable.

3. An unmanned vehicle which comprises a group of components which consist of at least one of the following components: health detection means for determining the health of individual animals in a herd of animals, and behavior monitoring means for monitoring the individual behavior of animals in said herd of animals, the vehicle further comprising an animal identification system which comprises a transmitter and a receiver, a radar reflector means worn by each said animal of said herd of animals, said transmitter and receiver comprising a radar.

4. An unmanned vehicle which comprises a group of components which consist of at least one of the following components: health detection means for determining the health of individual animals in a herd of animals, and behavior monitoring means for monitoring the individual behavior of animals in said herd of animals, the vehicle further comprising disinfecting means for disinfecting at least part of a stable for said animals of said herd of animals.

5. A vehicle in accordance with claim 4, wherein said disinfecting means is disposed on a telescopic carrier.

6. An unmanned vehicle which comprises a group of components which consist of at least one of the following components: health detection means for determining the health of individual animals in a herd of animals, and behavior monitoring means for monitoring the individual behavior of animals in said herd of animals, the vehicle being in a stable which contains at least one of said animals of said herd of animals and further comprises disinfecting means for disinfecting at least part of said one animal in said stable.

7. A vehicle in accordance with claim 6, wherein said disinfecting means is disposed on a telescopic carrier.

8. An unmanned vehicle which comprises a group of components which consist of at least one of the following components: health detection means for determining the health of individual animals in a herd of animals, and behavior monitoring means for monitoring the individual behavior of animals in said herd of animals, the vehicle being disposed within a stable wherein manure is lying on a floor of said stable, the vehicle further comprising a manure slide for removing said manure lying on said floor in said stable.

9. An unmanned vehicle which comprises a group of components which consist of at least one of the following components: health detection means for determining the health of individual animals in a herd of animals, and behavior monitoring means for monitoring the individual behavior of animals in said herd of animals, the vehicle having a rotatable upper part, said health detection means being mounted on said upper part.

10. An unmanned vehicle which comprises a group of components which consist of at least one of the following components: health detection means for determining the health of individual animals in a herd of animals, and behavior monitoring means for monitoring the individual behavior of animals in said herd of animals, the vehicle comprising a rotatable upper part, said behavior monitoring means being mounted on said upper part.

11. An unmanned ground engaging mobile vehicle that moves proximate to animals of a herd of animals, such vehicle comprising observation means for observing each animal in said herd of animals, identification means for identifying each animal in said herd of animals, health detection means for determining the health of individual animals in said herd of animals, and behavior monitoring means for monitoring the individual behavior of animals in said herd of animals.

12. A vehicle in accordance with claim 11, wherein said animal identification means comprises an animal identification system which includes parts for identifying each animal connected to each animal.

13. A vehicle in accordance with claim 12, wherein said animal identification system comprises a transmitter and a receiver.

14. A vehicle in accordance with claim 11, wherein said health detection means comprises a camera.

15. A vehicle in accordance with claim 14, wherein said camera comprises an infrared camera.

16. A vehicle in accordance with claim 11, wherein said behavior monitoring means comprises a camera.

17. A vehicle in accordance with claim 16, wherein said camera comprises an infrared camera.

18. A vehicle in accordance with claim 11, wherein said health detection means is mounted on a telescopic carrier.

19. A vehicle in accordance with claim 11, wherein said behavior monitoring means is mounted on a telescopic carrier.

20. A vehicle in accordance with claim 11, which further comprises herding means for herding animals in said herd of animals.

21. A vehicle in accordance with claim 20, wherein said herding means comprises an electric shock device.

22. A vehicle in accordance with claim 11, which comprises alarm means for alerting a supervisor when said health detection means determines that an individual animal of said herd of animals is ill.

23. A vehicle in accordance with claim 11, which further comprises alarm means for alerting a supervisor when said behavior monitoring means ascertains that the individual behavior of an animal in said herd of animals is abnormal.

24. A vehicle in accordance with claim 11, which further comprises a navigation means for guiding the movements of the vehicle.

* * * * *